(12) United States Patent
Fritz et al.

(10) Patent No.: US 6,172,367 B1
(45) Date of Patent: Jan. 9, 2001

(54) METHOD AND DEVICE FOR MEASURING ELECTROMAGNETIC WAVES EMANATING FROM A MELT

(75) Inventors: Ernst Fritz; Norbert Ramaseder, both of Linz (AT)

(73) Assignee: Voest-Alpine Industrieanlagenbau GmbH., Linz (AT)

( * ) Notice: Under 35 U.S.C. 154(b), the term of this patent shall be extended for 0 days.

(21) Appl. No.: 09/091,477
(22) PCT Filed: Dec. 19, 1996
(86) PCT No.: PCT/AT96/00255
  § 371 Date: Jun. 19, 1998
  § 102(e) Date: Jun. 19, 1998
(87) PCT Pub. No.: WO97/22859
  PCT Pub. Date: Jun. 26, 1997

(30) Foreign Application Priority Data

Dec. 20, 1995 (AT) .................................... 2081/95

(51) Int. Cl.[7] .................. G01J 5/04; G01J 5/08; G01N 33/20; C21C 5/46
(52) U.S. Cl. .................. 250/341.6; 250/372; 250/341.1; 266/265; 266/216; 266/99
(58) Field of Search .................. 250/341.2, 341.6, 250/341.8, 347, 353, 372, 395, 491.1, 526; 75/382, 385; 374/139, 140; 164/4.1, 150.1, 151.4; 266/100, 99, 216, 265, 268

(56) References Cited

U.S. PATENT DOCUMENTS 3,161,499  12/1964  Percy .
3,659,944  *  5/1972  Bojic ..................................... 356/313

(List continued on next page.)

FOREIGN PATENT DOCUMENTS 1408873    11/1968  (DE) .
4025909 A1  7/1991  (DE) .

(List continued on next page.)

OTHER PUBLICATIONS

Japanese Abstract: Laser Emission Spectroscopic Analyzer of Molten Metal, JPA–145932, Aug. 21, 1984.

(List continued on next page.)

Primary Examiner—Constantine Hannaher
Assistant Examiner—Albert Gagliardi

(57) ABSTRACT

In a method for determining electromagnetic waves originating from the interior of a melt (3), in particular a metal melt, a gas-filled hollow space (26) is formed within the melt (3) by blowing in gas and electromagnetic waves emitting from the melt (3) are observed through the blown-in gas and evaluated by feeding the electromagnetic waves via an optical system (20) to a detector (22) for determining the temperature and/or chemical composition.

In order to avoid falsifications of the measured values, the emitting electromagnetic waves are cleared from electromagnetic waves (36, 37, 39, 40) directed obliquely to the optical axis (38) of the optical system (20) and present beyond a limit radius (41) drawn from the optical axis (38) of the optical system (20), by refracting said electromagnetic waves (36, 37, 39, 40) away from the optical axis (38) of the optical system (20) in a wave dispersion means (42) of the optical system (20) and only electromagnetic waves directed approximately parallel to the optical axis (38) of the optical system (20) arrive at a detector (22) arranged to follow the optical system (20), and/or the optical system (20) is moved relative to the hollow space (26) while adjusting its optical axis (38), until the intensity of the emitting electromagnetic waves yields a maximum during evaluation of the same (FIG. 2).

31 Claims, 5 Drawing Sheets

U.S. PATENT DOCUMENTS

| | | |
|---|---|---|
| 4,619,533 | 10/1986 | Lucas et al. . |
| 4,830,601 | 5/1989 | Dahlander et al. . |
| 5,397,108 * | 3/1995 | Alexander et al. ............... 266/100 |
| 5,447,373 * | 9/1995 | Okuhara ............................. 374/131 |
| 5,655,838 * | 8/1997 | Ridley et al. ....................... 374/130 |
| 5,785,426 * | 7/1998 | Woskov et al. .................... 374/126 |
| 5,830,407 * | 11/1998 | Cates ................................... 266/44 |

FOREIGN PATENT DOCUMENTS

| | | |
|---|---|---|
| 0162949A1 | 12/1985 | (EP) . |
| 0215483A2 | 3/1987 | (EP) . |
| 0362577A2 | 4/1990 | (EP) . |
| 0646778A1 | 4/1995 | (EP) . |
| 2514894 | 10/1981 | (FR) . |

OTHER PUBLICATIONS

Japanese Abstract: Laser Emission Spectral Analysis Method and Apparatus for Molten Metal, JPA2–254345, Oct. 15, 1990.

Japanese Abstract: Continuously Measuring Apparatus of Temperature of Melt in Refining Vessel, JPA60–61633, Apr. 9, 1985.

* cited by examiner

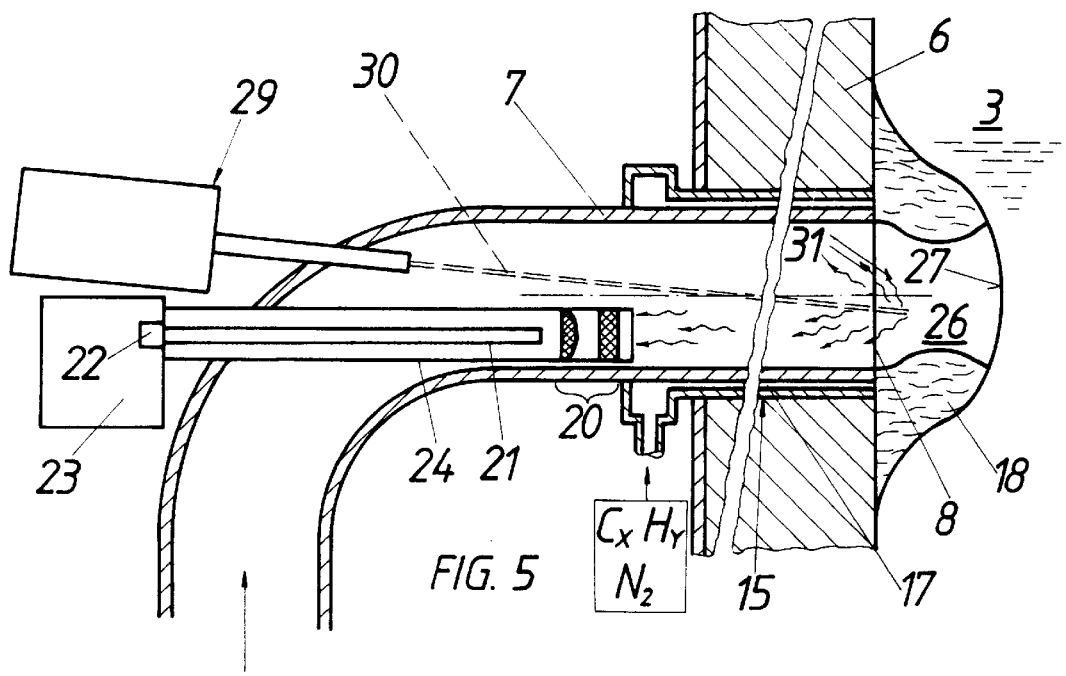
FIG. 5
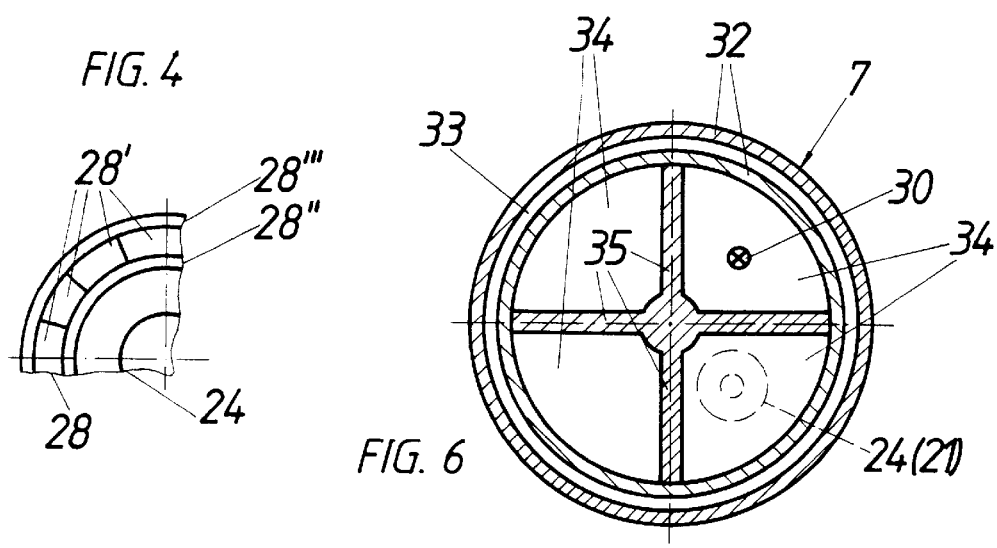
FIG. 4
FIG. 6

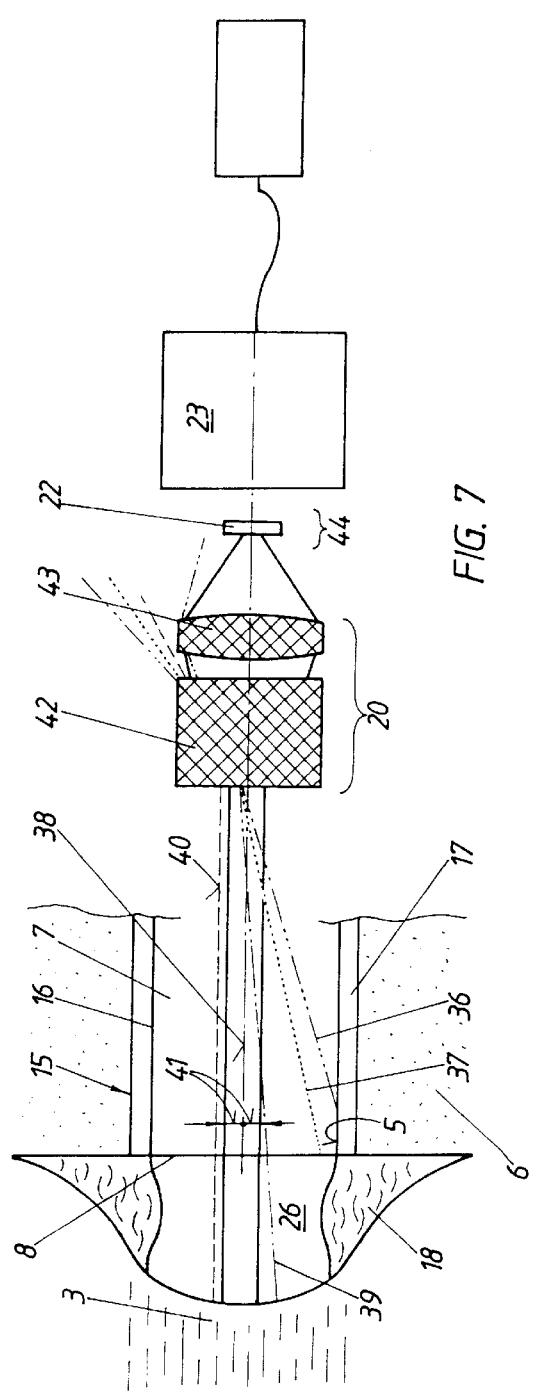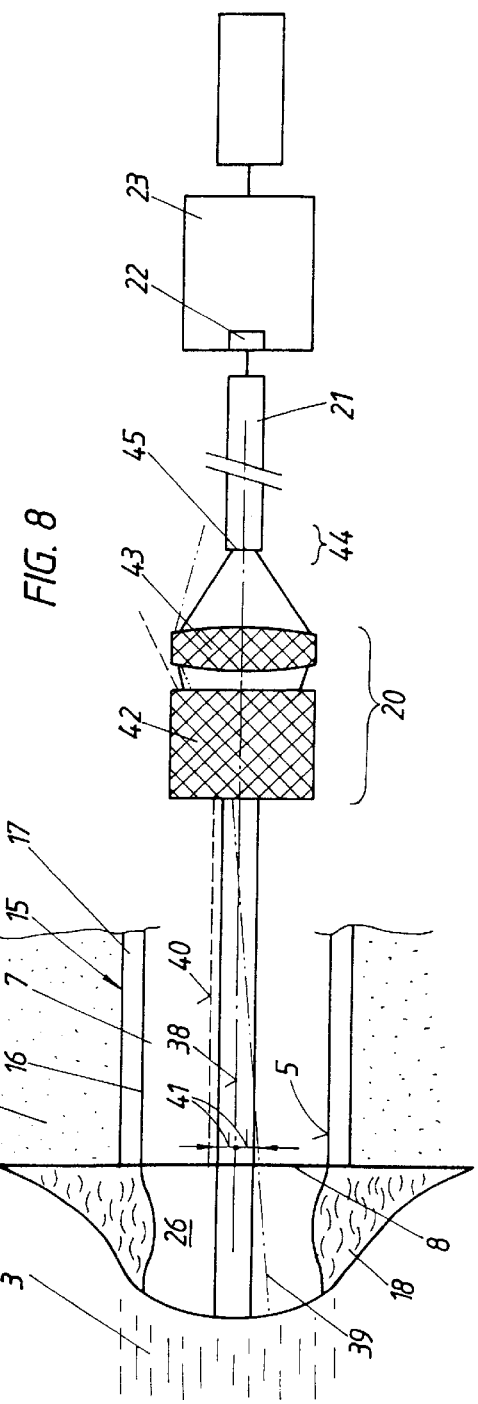

METHOD AND DEVICE FOR MEASURING ELECTROMAGNETIC WAVES EMANATING FROM A MELT

This application is the national phase under 35 U.S.C. §371 of prior PCT International Application No., PCT/AT96/00255, which has an International filing date of Dec. 19, 1996, which designated the United States of America, the entire contents of which are hereby incorporated by reference.

BACKGROUND OF THE INVENTION

1. Field of the Invention

The invention relates to a method for determining electromagnetic waves originating from the interior of a melt, in particular a metal melt, especially in the visible light range and the adjacent UV range and infrared range, wherein a gas-filled hollow space is formed within the melt by blowing in gas and electromagnetic waves emitting from the melt are observed through the blown-in gas and evaluated by feeding the electromagnetic waves via an optical system to a detector for determining the temperature and/or chemical composition, as well as an arrangement for carrying out the method.

2. Related Background Art

In the production of steel in a converter or any other metallurgical reactor by refining pig iron or treating other melts in such a metallurgical vessel, it has always been endeavoured to have available as continuously and quickly as possible the temperature values of the melt and/or an analysis of the melt during the active treatment process in order to be able to keep the treatment process as short as possible and to get as near as possible to the target analysis sought. Rapidity is required, in particular, because the chemical reactions proceed at high speeds, involving the danger of being no longer able to interfere with the refining process or treatment process in due time. The extremely rough operating conditions prevailing in such plants do not meet with these objects. In the production of steel in a metallurgical reactor (converter, electric furnace, etc.), in the secondary metallurgical treatment of steel melts or in respect of any other non-ferrous metal melts (e.g., Cu, Ni, Al) it is, furthermore, advantageous to know the temperature and/or analysis of the melt after each treatment stage.

To solve these problems, attempts have, for instance, been made to get hints as to the correct point of time for terminating a refining process from the spectral analysis of the converter flame or from its absorptive effect relative to monochromatic light of a defined wave length. However, the strongly varying blowing conditions and the foaming slag on the melt bath as well as the high content of dust contained in the offgas do not allow for sufficiently precise conclusions on the temperature of the bath and the analysis of the melt.

Furthermore, it had been proposed for temperature measuring (DE-B-14 08 873) to insert into the refractory lining of the converter encapsulated thermocouples, which project into the converter interior and in the operating position of the converter come to lie below the meniscus of the melt to be refined. However, the durability of such thermocouples was insufficient; in addition, measuring results have been adversely affected by the necessarily strong cooling of the measuring device.

Furthermore, it is known to determine the temperature of a melt at a predetermined point of time by means of lances submerged in the melt. That method is disadvantageous if applied to the production of steel in a converter, because to that end the converter must be tilted and set right again, which involves a temperature loss of the steel bath of up to 40° C. In addition, that method is time-consuming, because at first the blowing lance must be extended prior to tilting the converter and the converter must be set right again after having carried out a measurement, and it is only afterwards that the blowing lance—if necessary—can be retracted and blowing can be continued. Further drawbacks include that the measuring point within the melt may be chosen only arbitrarily, thus being hardly reproducible. Also the depth of immersion of the probe cannot be exactly determined, thus being hardly reproducible, either.

The determination of a chemical analysis of the melt is even substantially more complicated. To this end, it is known to take samples by means of lances submerged in the melt. When producing steel in a converter this involves disadvantages since the taking of such samples likewise requires much time—the converter likewise having to be tilted (except with perpendicular sublance measurements)—and the samples must be sent to the laboratory.

When producing steel in a converter it is known to carry out a quick carbon analysis by measuring the arrest point of the temperature and the C content. Thereby, it is however only feasible to acquire the C equivalent such that some of the accompanying elements present in the melt have to be taken into account when calculating the actual carbon content.

Furthermore, it is known to carry out carbon and oxygen activity analyses and to take samples and temperature measurements in a converter by means of sub lances. This is, however, disadvantageous inasmuch as the sublance means themselves (and also the samples) are very expensive, prone to extremely high wear and applicable only with liquid slags towards the end of a blowing process.

From EP-B-0 162 949 a method for observing the formation of slag in a steel blowing converter, using the light radiation emitted from the slag surface within the converter space is known. There, the light is photoelectrically converted into signals and processed, variations of the signals being taken as criteria of foamed slag formation. The receptors inserted in the side wall of the converter are located above the slag/melt bath and are not suitable for measuring the melt bath temperature and the melt composition.

From U.S. Pat. No. 4,830,601 a method and an arrangement for the spectral-analytical evaluation of the light emitted from the central portion of a burner flame is known. There, the supply of fuel and combustion air is surveyed by way of the light spectrum. Emitted light is transmitted to an electronic evaluation device via fiber-optic conductors, the supply of combustion air and fuel being controlled as a function of the gas analysis made.

A similar arrangement for temperature measurement in a process for producing reducing gas in a high-temperature reactor at an elevated operating pressure is to be taken from DE-A-40 25 909.

From EP-A-0 214 483 it is known to verify the chemical composition of iron by blowing oxygen or an oxygen-containing gas from top onto the surface of molten iron, wherein beams originating from the melt surface are detected in a spectrometer with a view to determining the chemical composition of the iron.

From U.S. Pat. No. 4,619,533 and EP-A-0 362 577 methods of the initially defined kind are known, wherein in the first case radiation originating from the metal melt is conducted to a detector via a fiber-optic waveguide. According to EP-A-0 362 577 laser light is focussed on the metal surface thus generating plasma. The plasma light emitted from the metal surface via a lens system and a fiber-optic waveguide is fed to a spectrometer for elementary analysis. The lens system comprises adjustable lenses. The lenses are adjusted in a manner that the ratio of the intensities of two iron lines, namely the intensity of an atomic line arid the intensity of a ionic line, is minimal.

In a method of the initially defined kind, i.e., when detecting electromagnetic waves originating from the interior of a melt, the blowing in of gas for the formation of a gas-filled hollow space advantageously is effected through a wall opening of a metallurgical vessel receiving the metal melt, said opening having to be located below the standard meniscus. In the region of transition of said opening of the metallurgical vessel towards the melt, i.e., in the marginal region of said opening, reflections of the electromagnetic waves emitting from the melt are caused even with a very small opening, leading to falsifications of the measured values. If a mushroom-shaped incrustation is formed of solidified melt as a result of the blown-in gas, the incrustation having the shape of a bead surrounding the marginal region of the opening about the total periphery and oriented in the direction towards the melt constitutes a disturbing factor despite its protective function for the opening, constantly varying in size and position, whereby radiation originating from the surface of the incrustation or from the region of transition of the incrustation to the melt will falsify the measuring result. It has been shown that a precise measurement can be carried out only if radiation originating exclusively from the melt surface is received and transmitted to the detector. Reflections from the marginal region of the opening or from the incrustation are strongly disturbing, i.e., bring about falsifications of the measured values, without this being recognizable by any other indications.

SUMMARY OF THE INVENTION

The invention aims at avoiding the above drawbacks and difficulties and has as its object to provide a method of the initially defined kind, as well as an arrangement for carrying out the method, by which the determination of desired measured values of a melt (such as, e.g., steel, stainless steel, ferroalloys and melts of nonferrous metals) is feasible in a simple manner practically without time delay and, in particular, continuously as well as even with viscous to dry slags. Falsifications of the measured values caused by the measuring process itself and by the rough conditions of steelworks operation are to be reliably prevented, falsifications of the measured values having to be excluded even with the hollow space provided within the melt being kept very small.

In accordance with the invention this object is achieved in that electromagnetic waves directed obliquely to the optical axis of the optical system and originating from the marginal region of the hollow space are excluded from detection by clearing through optical manipulation the emitting electromagnetic waves from electromagnetic waves directed obliquely to the optical axis of the optical system and present beyond a limit radius drawn from the optical axis of the optical system, by refracting said electromagnetic waves away from the optical axis of the optical system in a wave dispersion means of the optical system, such as a dispersing and focussing lens system, and only electromagnetic waves directed approximately parallel to the optical axis of the optical system arrive at a detector arranged to follow the optical system, and/or in that the optical system is moved relative to the hollow space while adjusting its optical axis, until the intensity of the emitting electromagnetic waves yields a maximum during, evaluation of the same.

According to a preferred embodiment, the wave dispersion means is followed by a wave bundling means, such as a focussing lens or a focussing lens system, and the electromagnetic waves directed approximately parallel to the optical axis of the optical system are focussed by the wave bundling means and fed to the detector directly or via a fiber-optic waveguide, yet the oblique waves and those present beyond a limit radius are not covered by such focussing.

A further preferred embodiment is characterized in that both the wave dispersion means and the consecutively arranged wave bundling means are moved relative to the hollow space while adjusting their optical axis, until the intensity of the emitting electromagnetic waves yields a maximum in the evaluation of the same. Thereby it is feasible to still obtain optimum measuring results even with a particularly intensive crust formation and/or strongly unilateral crust formation, i.e., with melts being particularly prone to crust formation or with hollow spaces within the melt having small diameters.

To carry out a melt analysis, energy is suitably supplied to the melt through the gas-filled hollow space and a portion of the melt is evaporated by the energy supplied, the blown-in gas advantageously entering into a chemical reaction with the melt thus causing a portion of the melt to evaporate.

To protect the measuring procedure, the gas blown in to form the gas-filled hollow space, on the site of entering the melt, suitably is surrounded by a gas jacket or several gas jackets containing a hydrocarbon-containing protective medium, preferably mixed with inert gas. This will cause the formation of an incrustation of solidified melt ensuring the supply of gas and also allowing for substantially gentle treatement of the arrangement required for carrying out a measurement as well as a long service life of the same.

Simplification and acceleration of the method is provided if the determination of the temperature or chemical analysis of the melt is combined with precalculited or measured parameters, such as a carbon computation of the offgas analysis or a rough calculation of the analysis of the melt at the time of measuring, and, furthermore, if only the contents of individual elements of the melt, such as, e.g., the Mn, Cr, C contents with iron melts, etc. are determined, the contents of the other elements or compounds contained in the melt and also in the slag melt being calculated therefrom.

The accuracy of the method according to the invention may be enhanced in that during measurement a temperature as close as possible to the actual temperature of the melt is adjusted within the hollow space and/or immediately in front of it by introducing a gas mixture.

Preferably the chemical analysis of the melt is concertedly changed, and the melt or melt and slag are mixed thoroughly, by aid of a gas or several different gases introduced into the melt.

According to a preferred embodiment, the gas-filled hollow space is formed on the upper surface of the melt, for instance, by a gas feed duct including an optic device, a fiber-optic waveguide, a detector, etc. immersing into the melt.

An arrangement for carrying out the method, comprising
  a vessel receiving a melt,
  a gas supply duct leading to an opening of the vessel and including a gas outlet opening oriented towards said opening and hence towards the melt, an optical system for observing the gas outlet opening, a detector for registering electromagnetic waves emitting from the melt, and optionally a waveguide conducting the electromagnetic waves to the detector, is characterized by an optical wave dispersion means, such as a dispersing-focussing lens system and/or by the optical system being arranged so as to be movable, preferably pivotable, relative to the metallurgical vessel.

A preferred embodiment is characterized by a wave bundling means arranged to follow the wave dispersion means, such as a focussing lens or a consecutively arranged focussing lens system, and a detector located in the focussing zone of the wave bundling means or a fiber-optic waveguide arranged there and leading to a detector.

Advantageously, a protective tube is provided for the optical system, comprising a gas flushing means, in particular a gas flushing means cleaning the lens system on the front face. This is required, in particular, if solids, such as, e.g., slag formers, dusts, in particular coal dust, etc. are blown into the melt through the gas supply duct between the measuring periods.

Another preferred embodiment is characterized in that the wave dispersion means is pivotable relative to the gas outlet opening oriented towards the melt, the point of intersection of the optical axis of the wave dispersion means with the cross sectional area of the gas outlet opening being adjustable within the cross sectional area thereof.

Suitably, both the wave dispersion means and the wave bundling means are mounted so as to be pivotable, the pivotable mounting advantageously being realized by a cardanic mounting.

In the focussing region of the wave bundling means there is provided either an inlet of a fiberoptic waveguide or the detector.

A suitable embodiment is characterized in that the end of the gas supply duct is configured as a double- or multi-tube nozzle whose jacket annular space(s) is (are) Connectable to a duct feeding a hydrocarbon gas. As a result, a crust of solidified melt is formed, which surrounds the gas inlet opening in a manner that the multi-tube nozzle will be arranged in a well protected manner at the vessel, i.e., in the brickwork of the vessel.

Preferably, the end of the gas supply duct is formed by a multi-channel nozzle whose nozzle openings are connectable to one or several supply ducts for hydrocarbon, carbon monoxide, carbon dioxide, inert gas, vapour, oil or water and/or mixtures thereof. As a result, the durability of the jacket nozzle and the accuracy of the measurement may be optimized while carrying out the measuring procedure and in general by adjusting the amount and/or composition of the gases or liquids introduced through the annular gaps.

According to a preferred embodiment device oriented towards the gas outlet opening of the gas supply duct is provide, as known per se from EP-A-0 362 577, a focussing means suitably being associated with the laser beam device.

Preferably, a gas supply duct comprising a wave dispersion means and immersing into the melt is provided.

A method of operating an arrangement according to the invention is characterized in that, for protecting that part of the arrangement which reaches into the vessel, the supply of the protective medium is controlled by continuously or step-wisely increasing the supply of hydrocarbon-containing protective medium with the attack of the melt increasing, i.e., with the temperature increasing of the melt being overheated.

BRIEF DESCRIPTION OF DRAWINGS

In the following the invention will be explained in more detail by way of several exemplary embodiments schematically illustrated in the drawing, wherein FIG. 4 depicts a special embodiment in an illustration analogous to FIG. 3.

FIGS. 5 and 6 each present sections transverse to the plane of FIG. 2 according to further embodiments.

FIGS. 7 and 8 schematically illustrate the beam paths according to the invention.

DETAILED DESCRIPTION OF PREFERRED EMBODIMENTS

Figure 1:
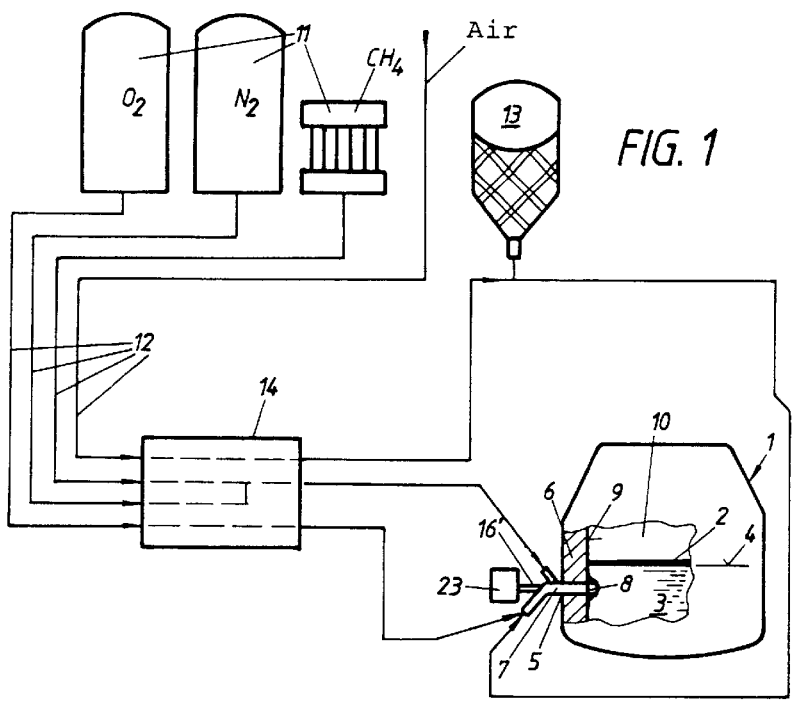
FIG. 1 is a (partially sectioned) schematic overall view of the arrangement according to the invention and FIGS. 2 and 3 each show a detail of FIG. 1 on an enlarged scale in different configurations

A metallurgical vessel 1, for instance, a refractorily lined converter (a vacuum vessel or an electric furnace or any other reactor, etc. might be provided as well) adapted to receive a steel melt 3 covered by a slag layer 2, at a height located below the meniscus 4 of the steel melt 3 with the converter 1 being normally filled, has an opening 5 in a side wall 6, in which opening a gas supply duct 7 is inserted, which opens into the interior 10 of the converter 1 on the inner side 9 of the side wall 6 of the same by a gas outlet opening 8. Different gases, e.g., oxygen, nitrogen, air, natural gas or mixtures thereof, as well as optionally also solids, e.g., dusty carbon and/or slag formers and/or dusts, may be introduced through the gas supply duct 7, the gases mentioned optionally acting as carrier gases for the solids. The gases are stored in tanks 11 and are withdrawn via ducts 12 upon demand. The solids are stored in one or sevel conveying vessels 13 or are withdrawn from existing systems and supplied to the converter 1 by aid of a conveying gas, such as air according to FIG. 1. The composition of the gases and the choice and quantitative adjustment of the gases may be effected by aid of a schematically illustrated valve stand 14.

Figure 2:
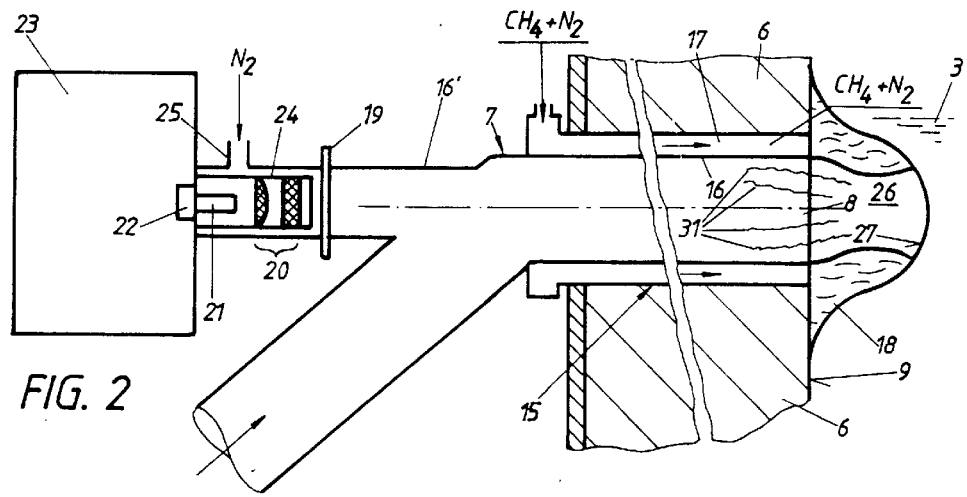

According to the embodiment illustrated in FIG. 2, the end of the gas supply duct 7 is designed as a jacket nozzle 15, wherein a hydrocarbon gas, optionally mixed with nitrogen, is introduced into the converter 1 through an annular gap 17 surrounding a central tube 16 of the jacket nozzle, thereby inducing the formation of an annular incrustation 18 protecting the mouth of the jacket nozzle 15 as a result of crack reactions. The end of the gas supply duct 7 also may be designed as a simple tube (without protective gas jacket) if durability is no point.

A branch tube 16' arranged in the direction of the axis of the jacket nozzle 15 and in alignment therewith, which is equipped with a screen 19 that may be provided with several adjacently arranged passage openings for the electromagnetic waves, opens into the central tube 16. Behind the screen 19, there are provided an optical system 20 acting as a focussing lens and behind the optical system 20 the end of a fiber-optic waveguide 21, for instance, a glass fiber conductor. The fiber-optic waveguide 21 leads to a detector 22 responding to electromagnetic waves and coupled with an amplifier and an electronic evaluation device 23.

The fiber-optic waveguide 21 and the optical system 20 advantageously are installed in a protective tube 24. Suitably, inert gas may be injected into the branch duct 16' via a duct 25, thus ensuring the optical system 20 to be kept free of dust.

The arrangement functions in the following manner:

To carry out a temperature measurement, just gas—no solids—, preferably inert gas, is blown into the converter 1 through the gas supply duct 7. In doing so, the gas pressure causes the formation of a hollow space 26 filled by that gas, which follows immediately upon the annularly formed incrustation 18, thus being delimited by the same and by the melt surface 27. The free passage opening for the gas safeguarded by the incrustation 18 is expected to have a minimum dimension of approximately 0.2 to 1.0 cm$^2$.

From the melt surface 27 of the melt 3 delimiting the gas-filled hollow space 26 electromagnetic waves are emitted, in particular, in the visible light range and in the UV range. These electromagnetic waves, via the opened screen or flap 19 and the optical system 20, get to the fiber-optic waveguide 21 and, via the latter, reach the detector 22. An electronic evaluation device 23 enables the determination of the temperature that is equivalent to the electromagnetic waves emitted in a natural way.

Figure 3:
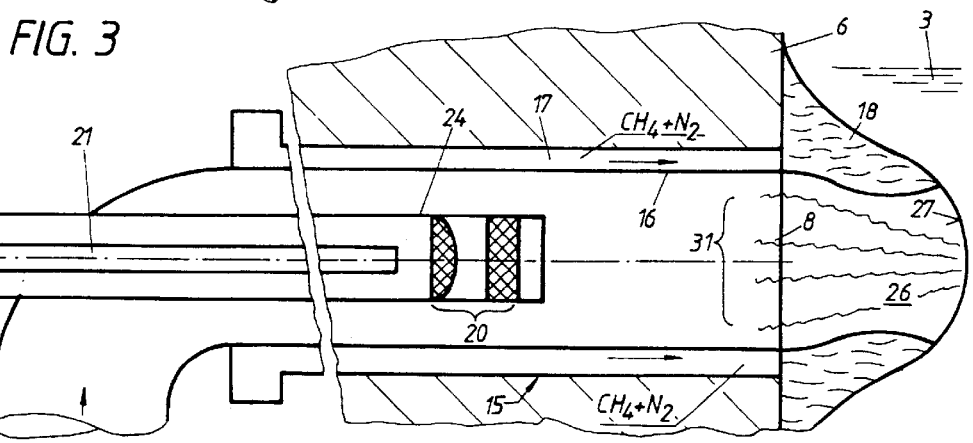

According to the embodiment represented in FIG. 3, the protective tube 24 together with the fiber-optic waveguide 21 directly projects into the gas supply duct 7 n the region of its end designed as a jacket nozzle 15. The protective tube 24 may be flushed with nitrogen, which, however, is not illustrated in detail.

According to FIG. 4, which depicts a section transverse to the longitudinal extension of a gas supply duct, the gas supply duct 7 in its end region is configured as a multi-channel nozzle. In the center of the multi-channel nozzle, the protective tube 24 and the optical system 20 including the fiber-optic waveguide 21 are provided. The protective tube 24 is peripherally surrounded by two annular gap volumes 25, 26 provided at a radial distance from each other, through which, for instance, hydrocarbon gases may be injected into the converter 1.

The further annular gap volume 28 provided between the two annular gap volumes 28" and 28'" is subdivided into several channels 28' by means of radial webs, said channels each extending over a partial peripheral region, viewed in cross section. Through these channels 28' other gases, such as, for instance, oxygen, inert gas or mixtures thereof, may be introduced into the converter.

FIG. 5 depicts a measuring arrangement according to the invention, comprising a laser beam device 29, which may be used for carrying out a melt analysis. In this case, the protective tube 24 including the fiber-optic waveguide 21 is installed slightly eccentrical of the gas supply duct 7. The laser beam 30 generated by the laser beam device 29 is oriented obliquely in the direction towards the gas outlet opening 8 so as to pass through approximately the center of the gas outlet opening 8, thus evaporating melt in the converter interior at the transition: gas bubble—liquid. The electromagnetic waves 31 emitting from the evaporated melt, which in FIG. 5 are indicated by wavy arrows, are detected by the fiber-optic waveguide 21 and evaluated by means of the electronic evaluation device 23. Preferably, the laser beam 30 is focussed through a focussing lens, a focal spot being formed at the opening 5 between the gaseous and liquid surfaces of the melt 3. Suitably, the arrangement is devised so as to be movable in the beam direction, thereby ensuring the optimum positioning of the focal spot. The gas supply duct 7 in its end region is configured as a jacket nozzle, hydrocarbon gases, inert gases or mixtures thereof being injected into the converter 1 through the annular space or annular gap 17.

FIG. 6 represents a cross section through the end region of a gas supply duct 7 according to a slightly modified form. The gas supply duct 7 externally is comprised of a double jacket 32, hydrocarbon gases, nitrogen, etc. being injected through the annular space 33 formed by the double jacket. The internal volume of the gas supply duct 7 is subdivided several times by means of walls 35 extending radially and in the longitudinal direction, i.e., into four spaced 34 of approximately equal size according to the exemplary embodiment illustrated. Through one of the spaces 34 the laser beam 30 is directed into the interior of the converter 1 and through a second space 34 the protective tube 24 comprising the lens system including the fiber-optic waveguide 21 passes. Each of the spaces 34 may be fed with different gases, for instance, with oxyen or inert gas or mixtures thereof.

From FIGS. 7 and 8, the beam paths preferred according to the invention and illustrated schematically are apparent. Electromagnetic waves 36 originating from the marginal region 35 of the hollow space 26 and of the opening 5, respectively, and, in particular, electromagnetic waves 37 reflected from the incrustation 18 as well as electromagnetic waves 39 propagating obliquely to the optical axis 38 of the optical system 20 and electromagnetic waves 40 present beyond a limit radius 41 drawn from the optical axis 38 of the optical system 20 are excluded from detection by said electromagnetic waves being refracted away from the optical axis 38 of the optical system 20 by means of a wave dispersion means 42 configured, for instance, as a dispersing and focussing lens system.

The wave dispersion means 42 is followed by a wave bundling means 43 by which the electromagnetic waves oriented approximately parallel to the optical axis 38 of the optical system 20 are focussed. The electromagnetic waves 39, 40 oriented obliquely to the optical axis 38 of the optical system 20 and present beyond a limit radius 41 drawn from the optical axis 38 of the optical system 20 are, however, not covered by such focussing.

The difference between the variant illustrated in FIG. 7 and the variant illustrated in FIG. 8 is to be seen in that once the detector 22 is located directly in the focussing zone 44 of the wave bundling means 43 (FIG. 7) and once, according to FIG. 8, an inlet 45 of a fiber-optic waveguide is located in the focussing zone, leading to a detector comprising an electronic evaluation device.

Figure 9:
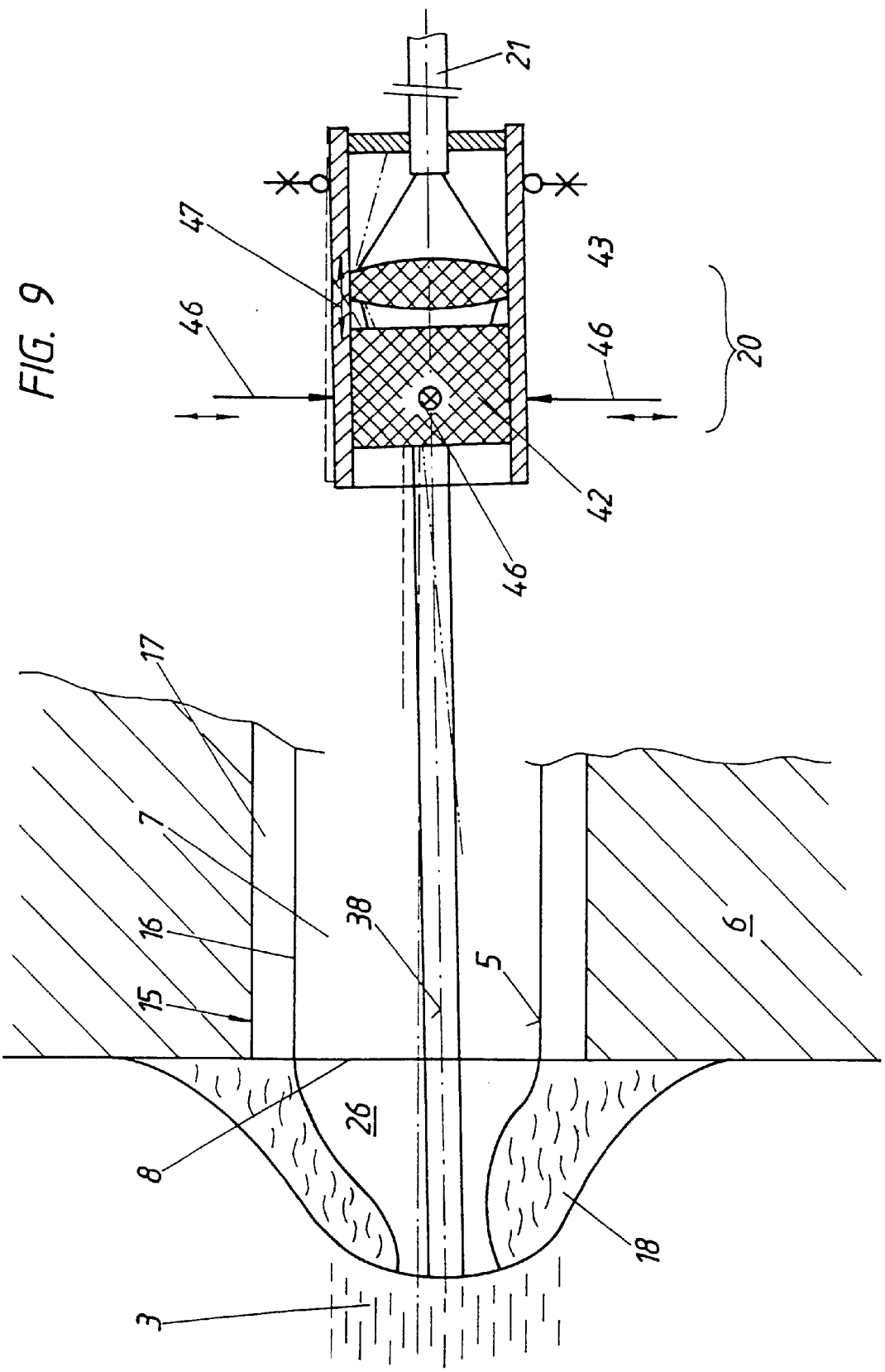
FIG. 9 depicts a preferred embodiment in an illustration analogous to FIG. 3.

According to the embodiment illustrated in FIG. 9, the optical system 20—which preferably comprises a wave dispersion means 42 and a wave bundling means 43—is pivotably mounted in the central tube 16, preferably in a manner that every point within the cross section of the opening 5 can be reached by the optical axis of the optical system 20. Such a movable mounting may be realized by means of several pressure-medium cylinders 46 engaging at the optical system and indicated by arrows in FIG. 9 or by means of a cardanic mounting. Thereby, it is feasible to adjust the optical axis 38 of the optical system 20 in a manner that it may be directed towards the melt 3 even with a unilateral growth of incrustation as illustrated in FIG. 9, falsifications of the measured values caused by the incrustation 18 thus being avoidable. In this case, the optical system 20 is pivoted until the intensity of the emitting electromagnetic waves yields a maximum during evaluation of the same. This constitutes a criterion that the optical axis of the optical system 20 is actually directed towards the melt 3 and not, for instance, towards the marginal region of the incrustation 3 or the marginal region of the opening 5. Displacement of the optical system 20 may be effected by aid of an electromechanic drive automatically adjusting the optical system 20 in a manner that a maximum intensity will be developed. Furthermore, axial displaceability of the optical system 20 may also be provided as indicated by the double arrow 47, to which end electric motors or pressure-medium cylinders may likewise be provided.

Figure 10:
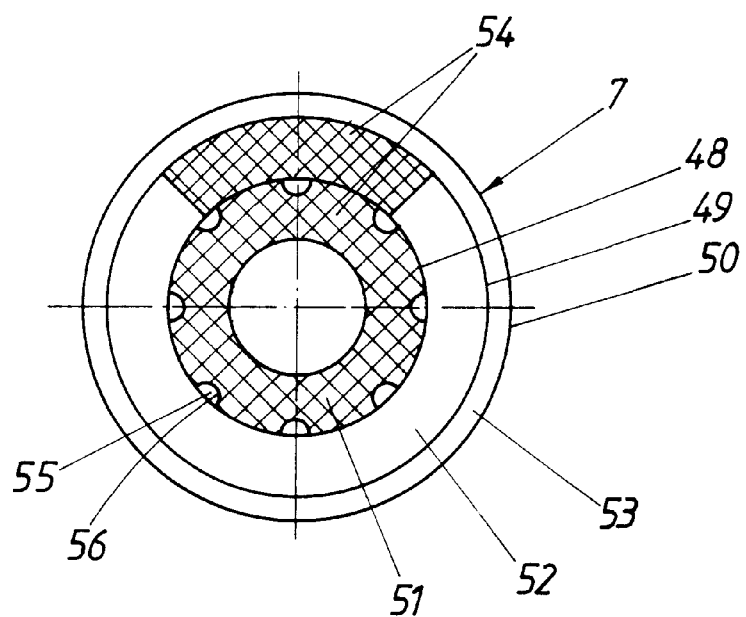
FIG. 10 represents a cross section through a gas supply tube in an illustration analogous to FIG. 4.

FIG. 10, in an illustration analogous to that of FIG. 4, shows a cross section through a gas supply tube comprised of four concentrically arranged cylindrical tubes 24, 48, 49, 50, intermediate spaces 51, 52, 53 each being provided between the cylindrical tubes. The innermost tube 24 serves as a gas supply tube for carrying out the measurement. There the optical system 20 and the fiber-optic waveguide 21 as well as optionally the detector 22 are provided. The intermediate space 51 radially following thereupon between the cylindrical tubes 24 and 48 is filled with refractory material 54, wherein grooves 55 are yet provided on the external periphery of the refractory material, which are lined with sheet metal coverings 56, if desired. Protective gas, e.g., $CH_4$, $CH_4+N_2$, etc., is directed to the end of the gas supply duct 7 through these grooves. The annular space 52 radially following thereupon, in the circumferential direction is filled with refractory material 54 by approximately one fourth, the remaining three fourths of the annular space 52 being free and serving to feed oxygen or oxygen mixed with other gases. The radially outermost annular space 53, in turn, serves to supply a protective gas.

Figure 11:
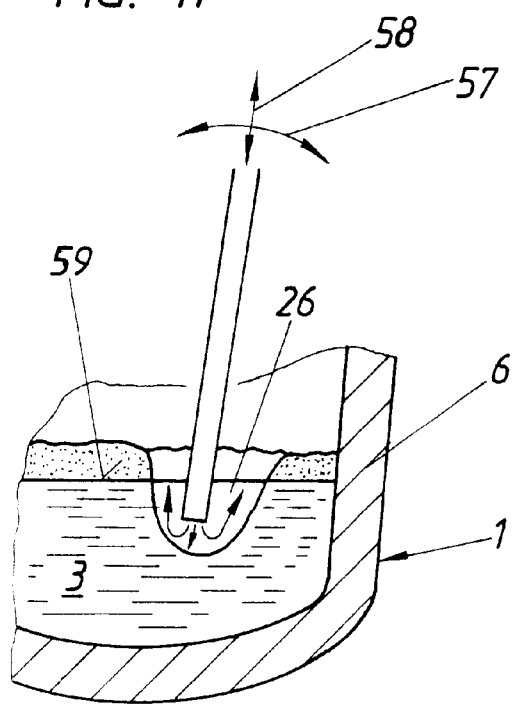
FIG. 11 relates to a further embodiment.

According to the embodiment represented in FIG. 11, a gas supply duct 7 in which the optical system 20 and the signal sensors (fiber-optic waveguide 21 and/or detector 22) are installed, by means of a displacement mechanism not illustrated in detail and al lowing for movements in the directions of the arrows 57, 58 indicated in FIG. 11, is moved from above into the melt 3 through the upper surface 59 of the same, thus causing a gas-filled hollow space 26 to form within the melt 3. Also in this case the end of the gas supply tube 7 may be configured as a jacket nozzle so as to form a protective gas jacket.

Measurements may be carried out according to two different basic principles, namely once by aid of a pyrometer and once by aid of a spectrometer. Evaluation subsequently is effected via special electronic evaluation devices that differ with respect to the two systems.

The radiation emitting in the case of a pure temperature measurement differs from that intended for a melt analysis. During a melt analysis the spectrum generated by a laser and emitted by a plasma is observed (UV range).

What is claimed is:

1. An apparatus for determining characteristics of a melt comprising:
   a vessel for receiving a melt,
   a gas supply duct leading to an opening of the vessel and including a gas outlet opening oriented towards said opening and hence towards the melt,
   an optical system for observing the gas outlet opening,
   a detector for sensing electromagnetic waves emitting from the melt, and
   a waveguide conducting the electromagnetic waves along an optical axis of the optical system to the detector,
   the optical system including an assembly for optically manipulating the electromagnetic waves emitted from the melt to constrain said detector to exclude electromagnetic waves oblique to the optical axis and to detect electromagnetic waves substantially parallel to the optical axis.

2. An apparatus according to claim 1, wherein said assembly includes an adjustment mechanism for moving the optical axis to a position where the detector senses only electromagnetic waves substantially parallel to the optical axis.

3. An apparatus according to claim 2, further including a dispersion device for refracting electromagnetic waves obliquely directed from the optical axis away from the detector.

4. An arrangement according to claim 3, further including a wave bundling apparatus arranged to follow the wave dispersion device, and a detector located in the focussing zone of the wave bundling apparatus.

5. An apparatus according to claim 4, wherein the focussing zone of the wave bundling apparatus is optically coupled to an inlet of a fiber-optic waveguide.

6. An apparatus according to claim 4, wherein the focussing zone of the wave bundling apparatus is optically coupled to the detector.

7. An apparatus according to claim 3, wherein the wave dispersion device is pivotable relative to the gas outlet opening oriented towards the melt, the point of intersection of the optical axis of the wave dispersion device with the cross sectional area of the gas outlet opening being adjustable within the cross sectional area thereof.

8. An apparatus according to claim 7, wherein both the wave dispersion device and the wave bundling apparatus are mounted so as to be pivotable.

9. An apparatus according to claim 8, wherein the pivotable mounting is realized by a cardanic mounting.

10. An apparatus according to claim 1, further including a protective tube provided for the optical system, comprising a gas flushing means for a front face of the optical system.

11. An apparatus according to claim 1, wherein the end of the gas supply duct is configured as a multi-tube nozzle with annular spaces therebetween connectable to a duct feeding a hydrocarbon gas.

12. An apparatus according to claim 1, wherein an end of the gas supply duct is formed by a multi-channel nozzle whose nozzle openings are connectable to one or several supply ducts for hydrocarbon gases.

13. An apparatus according to claim 1, further including a laser beam device oriented towards the gas outlet opening of the gas supply duct.

14. An apparatus according to claim 1, wherein said assembly comprises a dispersion device for refracting electromagnetic waves obliquely directed from the optical axis away from the detector.

15. An arrangement according to claim 14, further including a wave bundling apparatus arranged to follow the wave dispersion device, and a detector located in the focussing zone of the wave bundling apparatus.

16. An apparatus according to claim 15, wherein the focussing zone of the wave bundling apparatus is optically coupled to an inlet of a fiber-optic waveguide.

17. An apparatus according to claim 15, wherein the focussing zone of the wave bundling apparatus is optically coupled to the detector.

18. An apparatus according to claim 14, wherein the wave dispersion device is pivotable relative to the gas outlet opening oriented towards the melt, the point of intersection of the optical axis of the wave dispersion device with the cross sectional area of the gas outlet opening being adjustable within the cross sectional area thereof.

19. An apparatus according to claim 18, wherein both the wave dispersion device and the wave bundling apparatus are mounted so as to be pivotable.

20. An apparatus according to claim 19, wherein the pivotable mounting is realized by a cardanic mounting.

21. A method for determining characteristics of a melt comprising the steps of:

blowing gas into the melt to form a hollow space therein having marginal regions contiguous the melt;

feeding electromagnetic waves emitted from the interior of the melt through the hollow space formed in the melt to an optical analyzer system having an optical axis extending from a central region of said space to a radiation detector outboard of the hollow space;

optically manipulating electromagnetic waves emitted from the hollow space until a maximum intensity signal is sensed by the detector to thereby selectively detect electromagnetic waves traveling parallel to the optical axis, and selectively exclude electromagnetic waves emitted obliquely to the optical axis from said space; and determining characteristics of the melt by analyzing the electromagnetic waves sensed by the detector.

22. The method of claim 21 including the further steps of:

injecting a hydrocarbon-containing, protective, medium into the hollow space of the melt; and increasing the supply of said medium as the temperature of the melt increases.

23. The method of claim 21 wherein the electromagnetic waves selectively excluded from being sensed by the detector are refracted away from the optical axis by a wave dispersion device.

24. The method of claim 23 including the further steps of:

providing a focusing lens at an output side of the wave dispersion device; and selectively focusing electromagnetic waves substantially parallel to the optical axis along the optical axis to the detector.

25. The method of claim 24, wherein both the wave dispersion device and the focusing lens are disposed on the optical axis and are movable with the detector.

26. The method according to claim 21, wherein energy is supplied to the melt through the hollow space and a portion of the melt is evaporated by the energy supplied, in particular, by blown-in gas entering into a chemical reaction with the melt, thus causing a portion of the melt to evaporate.

27. The method according to claim 21, wherein the gas blown in to form the gas-filled hollow space on the site of entering the melt is surrounded by at least one gas jacket containing a hydrocarbon-containing, protective, medium mixed with inert gas.

28. The method according to claim 21, wherein the melt characteristics determined include the temperature and chemical composition of the melt.

29. The method according to claim 21, wherein during measurement a temperature as close as possible to the actual temperature of the melt is adjusted within the hollow space and immediately in front of it by introducing a gas mixture.

30. The method according to claim 21, wherein the chemical composition of the melt is constantly changed, and the melt and slag therein are mixed thoroughly, by aid of at least one gas introduced into the melt.

31. The method according to claim 21, wherein the hollow space is formed on an upper surface of the melt.

* * * * *